United States Patent
Liu et al.

(10) Patent No.: US 8,329,447 B2
(45) Date of Patent: Dec. 11, 2012

(54) **STRAIN OF *LACTOBACILLUS CRISPATUS***

(75) Inventors: Yang Liu, Mountain View, CA (US);
Rosa R. Yu, Sunnyvale, CA (US);
Andrew Cheng, San Jose, CA (US);
Qing Xia, Santa Clara, CA (US); Qiang Xu, Cupertino, CA (US)

(73) Assignee: Osel, Inc., Santa Clara, CA (US)

( * ) Notice: Subject to any disclaimer, the term of this patent is extended or adjusted under 35 U.S.C. 154(b) by 294 days.

(21) Appl. No.: 12/634,504

(22) Filed: Dec. 9, 2009

(65) Prior Publication Data

US 2010/0151026 A1 Jun. 17, 2010

Related U.S. Application Data

(60) Provisional application No. 61/271,646, filed on Jul. 20, 2009, provisional application No. 61/122,069, filed on Dec. 12, 2008.

(51) Int. Cl.
*C12N 1/20* (2006.01)
*A01N 63/00* (2006.01)

(52) U.S. Cl. ............................ 435/252.9; 424/93.45

(58) Field of Classification Search ............... 435/252.9; 424/93.45
See application file for complete search history.

(56) References Cited

OTHER PUBLICATIONS

Siciliano et al., Proteomic investigation of the aggregation phenomenon in *Lactobacillus crispatus* Biochimica et Biophysica Acta 1784 (2008) 335-342.*
Ngo, J. et al., "Computational Complexity, Protein Structure Prediction, and the Levinthal Paradox", 1994, The Protein Folding Problem and Tertiary Structure Prediction, Merz et al. (eds.), Birkhauser Boston: Boston, MA, 492-495.*
Kimchi-Sarfaty C et al., A "silent" polymorphism in the MDR1 gene changes substrate specificity.Science. Jan. 26, 2007;315(5811):525-8.*
Voet, Biochemistry, John Wiley and Sons, pp. 126-128. 1990.*
Cesena et al., *Lactobacillus crispatus* and its Nonaggregating Mutant in Human Colonization Trials 2001 J. Dairy Sci. 84:1001-1010.*

* cited by examiner

*Primary Examiner* — Maria Leavitt
(74) *Attorney, Agent, or Firm* — Kilpatrick Townsend & Stockton LLP

(57) ABSTRACT

The invention provides a naturally occurring strain of *Lactobacillus crispatus* with advantageous characteristics. The strain colonizes mucosal surfaces, particularly vaginal surfaces. The strain is also capable of rapid growth in a number of conditions and is highly viable after desiccation. Moreover, the strain is capable of preventing and reducing pathogenic infection of vaginal mucosa.

11 Claims, No Drawings

SEQUENCE LISTING

<160> NUMBER OF SEQ ID NOS: 2

<210> SEQ ID NO 1
<211> LENGTH: 819
<212> TYPE: DNA
<213> ORGANISM: Lactobacillus crispatus
<220> FEATURE:
<223> OTHER INFORMATION: nucleotide sequence unique to Lactobacillus crispatus strain SJ-3C

<400> SEQUENCE: 1

```
ggcctacaag acaaatccag agttgaataa ctttgtaaat cgaattatgc aaaaaggtac      60
tcctgaatat aacgctttag gtgatggtat tggtacattt caaaatactg ataccttagc     120
taaattttta cctaaattaa aggcgttagg aatggatagt gcgagaagtc ttaatgattt     180
agatgccttc agatataata atgtgaaaca gcacttcatt aatctaaaag aaagagatcc     240
caagaaagtc gcagatgaaa tctttaatgc ttatacaaga gaagaagaca acatagaactt     300
gagaacactt gaaggacata agataaaata tgcttatgct gctttaaaag ttagattcaa     360
taatgaggga gattatatcg atcacggttt ggaattaaac tttaccgttg taggaagtta     420
ttcaccagaa tggattaagg cttgggaagc tgctaagtag aaattagaaa taaaggttaa     480
ttagttatgc taattgcctt tttttgttcc taaaaatgaa aataaaaaaa agtagattag     540
ctattaatca acagcgaaaa agtgataaaa agaaaaaaat tggtacaata gtagctattg     600
ttgcactaat tttaatcggg gttgcgattt actgtattgc aaactttaat catcttcaag     660
gaaaagctgc taactatgta gcaactaatc atttgtcgag tcaaagaaaa acaaacaga     720
agaaaaagcc aagttttaat atgaaggctg tccaacctgt atcacctcaa tctcttgcca     780
atgcatatca gcatagaaga gattatcgag ctgtaggcc                            819
```

<210> SEQ ID NO 2
<211> LENGTH: 1528
<212> TYPE: DNA
<213> ORGANISM: Lactobacillus crispatus

```
<220> FEATURE:
<223> OTHER INFORMATION: partial sequence of 16S rDNA of Lactobacillus
      crispatus strain SJ-3C

<400> SEQUENCE: 2
agagtttgat catggctcag gacgaacgct ggcggcgtgc ctaatacatg caagtcgagc      60
gagcggaact aacagattta cttcggtaat gacgttagga aagcgagcgg cggatgggtg     120
agtaacacgt ggggaacctg ccccatagtc tgggatacca cttggaaaca ggtgctaata    180
ccggataaga aagcagatcg catgatcagc tttaaaagg cggcgtaagc tgtcgctatg     240
ggatggcccc gcggtgcatt agctagttgg taaggtaaag gcttaccaag gcgatgatgc    300
atagccgagt tgagagactg atcggccaca ttgggactga gacacggccc aaactcctac    360
gggaggcagc agtagggaat cttccacaat ggacgcaagt ctgatggagc aacgccgcgt    420
gagtgaagaa ggttttcgga tcgtaaagct ctgttgttgg tgaagaagga tagaggtagt    480
aactggcctt tatttgacgg taatcaacca gaaagtcacg gctaactacg tgccagcagc    540
cgcggtaata cgtaggtggc aagcgttgtc cggatttatt gggcgtaaag cgagcgcagg    600
cggaagaata agtctgatgt gaaagccctc ggcttaaccg aggaactgca tcggaaactg    660
tttttcttga gtgcagaaga ggagagtgga actccatgtg tagcggtgaa atgcgtagat    720
atatggaaga acaccagtgg cgaaggcggc tctctggtct gcaactgacg ctgaggctcg    780
aaagcatggg tagcgaacag gattagatac cctggtagtc catgccgtaa acgatgagtg    840
ctaagtgttg ggaggtttcc gcctctcagt gctgcagcta acgcattaag cactccgcct    900
ggggagtacg accgcaaggt tgaaactcaa aggaattgac ggggccccgc acaagcggtg    960
gagcatgtgg tttaattcga agcaacgcga agaaccttac caggtcttga catctagtgc   1020
catttgtaga gatacaaagt tcccttcggg gacgctaaga caggtggtgc atggctgtcg   1080
tcagctcgtg tcgtgagatg ttgggttaag tcccgcaacg agcgcaaccc ttgttattag   1140
ttgccagcat taagttgggc actctaatga gactgccggt gacaaaccgg aggaaggtgg   1200
ggatgacgtc aagtcatcat gccccttatg acctgggcta cacacgtgct acaatgggca   1260
gtacaacgag aagcgagcct gcgaaggcaa gcgaatctct gaaagctgtt ctcagttcgg   1320
actgcagtct gcaactcgac tgcacgaagc tggaatcgct agtaatcgcg gatcagcacg   1380
ccgcggtgaa tacgttcccg ggccttgtac acaccgcccg tcacaccatg ggagtctgca   1440
atgcccaaag ccggtggcct aaccttcggg aaggagccgt ctaaggcagg gcagatgact   1500
ggggtgaagt cgtaacaagg taaccgta                                       1528
```

STRAIN OF *LACTOBACILLUS CRISPATUS*

CROSS REFERENCES TO RELATED APPLICATIONS

This application claims priority to U.S. patent application No. 61/122,069, filed Dec. 12, 2008, and U.S. patent application No. 61/271,646, filed Jul. 20, 2009, both incorporated herein by reference in their entireties.

BACKGROUND OF THE INVENTION

Lower genital tract infections, including sexually transmitted diseases (STDs) are some of the most common clinical problems among women of childbearing age. Vaginal discharge can be due to vaginal infections (yeast, bacteria, and trichomonas) or cervical infections (gonorrhea or chlamydia). Additionally, there is a body of evidence linking vaginal infections to preterm delivery, low birth weight, and neonatal mortality. Bacterial vaginosis is one of the most common genital infections in pregnancy. Women with bacterial vaginosis diagnosed during the second trimester of pregnancy are 40 percent more likely to give birth to a premature, low-birth weight infant than women without bacterial vaginosis. The prevention of even a small proportion of such births could translate into large monetary savings and a decrease in neonatal morbidity and mortality.

Lactobacilli are Gram positive rods that are a part of the microbial flora of the human mouth, gut, and vagina. Vaginal lactobacilli are thought to play an important role in resistance to infection via production of lactic acid and acidification of the vagina or by production of other antimicrobial products, such as hydrogen peroxide ($H_2O_2$). It has been demonstrated that women with predominant vaginal *Lactobacillus* flora have a 50% lower frequency of gonorrhea, chlamydial infections, trichomoniasis and bacterial vaginosis. The presence of $H_2O_2$-producing lactobacilli in the vagina have been linked to a decreased frequency of bacterial vaginosis, yeast vaginitis and sexually transmitted pathogens including *Neisseria gonorrhea*, *Chlamydia trachomatis*, and *Trichomonas vaginalis*. In vitro studies have demonstrated that $H_2O_2$-producing lactobacilli have potent bactericidal and viricidal properties against vaginal pathogens and even against human immunodeficiency virus (HIV) (see, e.g., Sha et al. (2005) *J Infect Dis* 191:25-32; Martin et al. (1999) *J Infect Dis* 180:1863-68).

Many women of childbearing age lack vaginal lactobacilli. The vaginal ecosystem is dynamically affected by medications, general health status, sexual practices, and contraception. Many vaginal and systemic medications may kill vaginal lactobacilli. Hence, treatment of sexually transmitted diseases with antibiotics may place women at increased risk for repeated acquisition of the diseases. These findings, along with the widespread belief that lactobacilli generally promote vaginal health, suggest that women should recolonize the vagina with *Lactobacillus* to prevent or treat genital tract infections.

*Lactobacillus* products for intravaginal or oral use have been available for over 100 years in the form of "acidophilus" preparations available in health food stores, and acidophilus milk or yoghurt bought in grocery stores (from *Lactobacillus acidophilus*). These products have included vaginal suppositories containing lyophilized *Lactobacillus acidophilus* or other *Lactobacillus* species of human origin as well as various nutritional supplements. These products have been largely non-efficacious due to the failure of the products to colonize the vagina with the exogenous lactobacilli, likely due to the poor quality of the commercially available products or the use of ecologically inappropriate strains. *Lactobacillus* food products or supplements are often contaminated with other potential pathogens. In addition, *Lactobacillus* obtained from yoghurt is often unable to bind to vaginal epithelial cells. Binding of lactobacilli to the mucosal surface is a necessary step to establish colonization of the host organism. Thus, commercially available *Lactobacillus* products generally have little utility in prevention or treatment of vaginal infection because the products contain inappropriate microbe strains, are contaminated with other potentially pathogenic organisms, have low viability, and/or do not have the ability to bind to vaginal mucosa and establish colonization.

BRIEF SUMMARY OF THE INVENTION

The invention provides a naturally occurring strain of vaginal *Lactobacillus crispatus* having a number of advantageous properties. Accordingly, the invention provides isolated *Lactobacillus crispatus* bacteria having distinguishing characteristics of a bacterial strain deposited under ATCC number PTA-10138. In some embodiments, the isolated bacterium comprises a polynucleotide sequence with at least 98% identity to the sequence of SEQ ID NO:1. In some embodiments, the bacterium comprises the polynucleotide sequence of SEQ ID NO:1.

In some embodiments, the invention provides a pharmaceutical composition comprising an isolated *Lactobacillus crispatus* bacterium having distinguishing characteristics of a bacterial strain deposited under ATCC number PTA-10138. In some embodiments, the bacteria are desiccated. In some embodiments, the bacteria are at least 40% viable upon rehydration from desiccated conditions. In some embodiments, the pharmaceutical composition is a dried formulation. In some embodiments, the pharmaceutical composition comprises a preservation matrix comprising at least a binding agent, an antioxidant, a polyol, a carbohydrate, and a proteinaceous material.

In some embodiments, the composition is in a single dose for vaginal delivery. In some embodiments, the single dosage form comprises at least $10^8$ viable bacteria of claim 1 for at least 12 months in vitro. In some embodiments, the single dosage form comprises at least $10^8$ viable bacteria of claim 1 for at least 12 months at a temperature of 4-6° C. In some embodiments, the single dosage form comprises at least $10^8$ viable bacteria of claim 1 for at least 12 months at room temperature.

In some embodiments, the invention provides the use of a substantially pure bacterial culture of at least $10^8$ bacteria of an isolated *Lactobacillus crispatus* bacterial strain having distinguishing characteristics of a bacterial strain deposited under ATCC number PTA-10138 in the preparation of a vaginal medicament for protecting a female from a vaginal infection. In some embodiments, the vaginal infection is an infection selected from the group consisting of bacterial vaginosis, yeast vaginitis, gonorrhea, chlamydia, trichomoniasis, urinary tract infection, pelvic inflammatory disease, herpes simplex virus type 2 (HSV-2), and human immunodeficiency virus (HIV) infection.

In some embodiments, the invention provides a method of reducing vaginal infection, the method comprising the step of contacting a vaginal mucosal surface with a composition comprising isolated *Lactobacillus crispatus* bacteria in an amount sufficient to reduce the survival of a vaginal infective agent, wherein the bacteria have distinguishing characteristics of a bacterial strain deposited under ATCC number PTA-10138. In some embodiments, the vaginal infective agent is selected from the group consisting of: yeast, pathogenic bacteria, gonorrhea, chlamydia, trichomoniasis, HSV-2 and HIV.

In some embodiments, the invention provides a method of reducing survival of yeast on a vaginal mucosal surface, the method comprising the step of contacting the mucosal surface with a composition comprising isolated *Lactobacillus crispatus* bacteria in an amount sufficient to reduce the survival of yeast on the vaginal mucosal surface, wherein the bacteria have distinguishing characteristics of a bacterial strain deposited under ATCC number PTA-10138.

In some embodiments, the invention provides a method of reducing the survival of pathogenic bacteria on a vaginal mucosal surface, the method comprising the step of contacting the mucosal surface with a composition comprising isolated *Lactobacillus crispatus* bacteria in an amount sufficient to reduce the survival of vaginosis-associated bacteria on the vaginal mucosal surface, wherein the *Lactobacillus crispatus* bacteria have distinguishing characteristics of a bacterial strain deposited under ATCC number PTA-10138.

The invention also provides a method of growing *Lactobacillus crispatus* bacteria, the method comprising the step of growing the bacteria with media comprising 10-30 mM magnesium, wherein the bacteria have distinguishing characteristics of a bacterial strain deposited under ATCC number PTA-10138.

In some embodiments, the invention provides a method of manufacturing a medicament for reducing vaginal infection, the method comprising packing at least $10^8$ bacteria of an isolated *Lactobacillus crispatus* strain having distinguishing characteristics of a bacterial strain deposited under ATCC number PTA-10138, in a single dosage form appropriate for vaginal delivery.

DETAILED DESCRIPTION OF THE INVENTION

The present invention provides a unique strain of that can be manufactured under exacting conditions while retaining high viability. The strain is naturally occurring, and colonizes vaginal mucosa well after desiccation, storage, and rehydration. Moreover, the strain has potent anti-microbial and anti-viral properties. This strain also carries a unique nucleotide tag that can be easily tracked, e.g., to reliably identify the strain. Thus the invention provides compositions and methods for preventing vaginal infections.

A. Definitions

*Lactobacillus* bacteria are Gram-positive facultative anaerobic bacteria, characterized by the ability to produce lactate (lactic acid) from carbohydrate sources such as glucose. These bacteria generally colonize vaginal and gastrointestinal mucosa. *Lactobacillus crispatus* refers to a species of the *Lactobacillus* genus. The species is generally distinguished from other lactobacilli based on the polynucleotide sequence of the ribosomal 16S ribosomal RNA.

The *Lactobacillus crispatus* SJ-3C strain of the invention includes bacteria having the distinguishing characteristics of the bacterial strain deposited under ATCC number PTA-10138. These SJ-3C bacteria include those essentially derived from the deposited parental strain, but may be slightly modified over serial passage, such that distinguishing characteristics are maintained. For example, with repeated culturing, or prolonged survival in situ, the strain can develop minor mutations that do not significantly affect the phenotype of the parent bacteria. For the purposes of this invention, *L. crispatus* SJ-3C includes cultures that are essentially derived from the deposited strain and retain at least five of the six distinguishing characteristics of the deposited strain, described herein.

The term "distinguishing characteristics" refers to characteristics of the *Lactobacillus crispatus* SJ-3C strain of the invention that distinguish it from other bacterial strains. SJ-3C bacteria, including those that are essentially derived from the *L. crispatus* strain deposited under ATCC number PTA-10138, can be identified based on these properties. Methods of detecting the distinguishing characteristics of SJ-3C bacteria are described herein.

The term "essentially derived" refers to bacteria that are derived from a parental strain and retain the distinguishing characteristics of the parental strain. Thus, except for the differences which result from derivation (e.g., from prolonged growth in culture or in situ), it conforms to the parental strain in the expression of characteristics that result from the genotype of the parental strain. As used herein, essentially derived bacteria refer to those derived from the *L. crispatus* strain deposited under ATCC number PTA-10138. An SJ-3C bacterium essentially derived from the deposited strain will retain at least 5 of the 6 distinguishing characteristics of the deposited strain.

The phrase "nucleic acid," "polynucleotide," or "polynucleotide sequence" refers to a single or double-stranded polymer of deoxyribonucleotide or ribonucleotide bases read from the 5' to the 3' end. Polynucleotides can also include modified nucleotides. Nucleic acid sequences include both DNA strand sequences, and RNA sequences, e.g., mRNA (for a coding sequence), rRNA, or tRNA. Polynucleotides can include both the full length nucleic acid sequences as well as non-full length sequences derived from the full length sequences.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

An algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available on the World Wide Web through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

The term "substantial identity" of polynucleotide sequences means that a polynucleotide comprises a sequence that has at least about 95% identity to a given reference sequence. Percent identity can be anywhere from 90% to 100%. Most embodiments include at least: 95%, 98%, or 99% compared to a reference sequence using the programs described herein (e.g., BLAST, using standard parameters). In the case of coding sequences, polynucleotide sequences include those that encode a polypeptide with substantial identity to a given reference sequence. One of skill will recognize that these values can be appropriately adjusted to determine corresponding identity of proteins encoded by two nucleotide sequences by taking into account codon degeneracy, amino acid similarity, reading frame positioning, etc.

As used herein, the terms "pharmaceutical composition" is used synonymously with physiologically acceptable and pharmacologically acceptable. A pharmaceutical composition will generally comprise agents for buffering and preservation in storage, and can include buffers and carriers for appropriate delivery, depending on the route of administration.

A "desiccated" or "dried" composition refers to a composition from which moisture has been removed. Desiccation techniques include, e.g., heating (e.g., sublimation), application of low pressure or vacuum, lyophilization (i.e., freeze drying), and combinations thereof. Pharmaceutical compositions are commonly desiccated for easy storage and transport, and can be rehydrated before administration.

As used herein, the term "viable" refers to a cell that is able to survive in a given condition (e.g., in culture or in situ). Viable cells are generally able to colonize and reproduce in the given condition. Percent viability refers to the percentage of viable cells in a population. For example, percent viability can refer to the percentage of *L. crispatus* in a pharmaceutical composition that will survive and colonize upon application to a mucosal surface. Viability can also be used in reference to viruses. A viable virus is one that is capable of infecting a target cell.

A "vaginal medicant" is a medicant (i.e., medicament or pharmaceutical composition comprising an active ingredient) which is used to prevent or treat infections, diseases, or other disorders directly or indirectly related to the vagina, including infections and diseases which can gain entry to the body through the vagina. Although a vaginal medicant of the present invention is primarily described herein for its use related to vaginal infections, it is to be understood that such a vaginal medicant can be used to treat related infections and conditions, such as oral and gastrointestinal infections. In such cases, the medicant of the present invention can be referred to as an oral or gastrointestinal medicant.

A "preservation matrix" comprises agents to minimize the damaging effects encountered during preservation. Generally, a L. crispatus strain is converted from an actively growing metabolic state to a metabolically inactive state upon addition to the preservation matrix for preservation. The preservation matrix can therefore be formulated for optimal cell resilience, such that the cells are immediately free to adhere to mucosal surfaces upon rehydration and return to full metabolic activity. A preservation matrix can comprise a biologically active binding agent, an antioxidant, a polyol, a carbohydrate and a proteinaceous material, as described in more detail herein.

The terms "dose" and "dosage" are used interchangeably herein. A dose refers to the amount of active ingredient (L. crispatus) given to an individual at each administration. The dose will vary depending on a number of factors, including frequency of administration; size and tolerance of the individual; severity of the condition; risk of infection; and the route of administration. For example, a single dose of the L. crispatus of the present invention can be in the range of $10^8$ to $10^9$ cells. The dose can, however, be modified depending on the above factors. This dose can also be used as a baseline, and modified based on the initial reaction of the individual.

A "dosage form" refers to the particular format of the pharmaceutical, and depends on the route of administration. For example, a dosage form can be in a suppository, e.g., for vaginal administration, a tablet or liquid, e.g., for oral delivery, or a saline solution, e.g., for injection. A "single dosage form" refers both to the format of the pharmaceutical composition and the amount of active ingredient (L. crispatus) as discussed above.

The term "isolated" is not an absolute term, but refers to a material that is substantially free of contaminants or components that accompany the material in its native state. An isolated L. crispatus strain can be accompanied by, e.g., pharmaceutically acceptable excipients, but will generally not include significant amounts of other bacterial species.

Similarly, "substantially pure" is not an absolute term, but refers to a composition that does not contain significant amounts of undesirable or contaminating substances.

"Protecting a female from a vaginal infection" refers to reducing the potential for a female to develop a vaginal infection. The term includes protection from further infection or worsening infection, e.g., in the case of an individual that is already suffering from a vaginal infection. The potential for a vaginal infection can be reduced to such an extent that the female does not suffer discomfort and/or altered function upon exposure to a vaginal infectious agent. For example, protecting a female from a vaginal infection can refer to the ability of a vaginal medicant of the present invention, when administered to the female, to prevent a vaginal infection from occurring or recurring.

"Treating" or "reducing" a vaginal infection refers to reducing the amount of the infective agent (e.g., number of cells or viral particles), reducing the severity of symptoms, and/or reducing the frequency of symptoms. In some embodiments, the number of infective agents is reduced by at least 10%, as compared, e.g., to the individual before administration or to a control individual not undergoing treatment. In some embodiments the number of infective agents is reduced by at least 25%, 50%, 75%, 80%, or 90%. In some embodiments, the infection is no longer detectable, e.g., by symptoms or general diagnostic techniques.

The term "infection" refers to the presence of a potentially pathogenic and undesirable agent in an individual. Infection does not necessarily imply that an infected individual will experience symptoms from the infective agent. Infective or pathogenic agents, for the purposes of the invention, include yeast (e.g., Candida, Cryptococcus, and Saccharomyces species), bacteria involved in bacterial vaginosis (e.g., Gardnerella and Mobiluncus), Trichomonas, Chlamydia, Neisseria gonorrhea, bacteria involved in urinary tract infections (e.g., E. coli, Staphylococcus, Chlamydia, and Mycoplasma), and viruses (e.g., HIV, human papilloma virus (HPV), hepatitis B virus, hepatitis C virus, HSV-2).

Mucosal surfaces include epithelial linings of the reproductive tract, gastrointestinal tract, oral and esophageal surfaces, nasal cavity, and bronchial lining. The L. crispatus of the present invention naturally colonizes the vaginal mucosal surface, but can be applied to other mucosal surfaces.

An "amount sufficient to reduce survival" of infective agents (e.g., yeast, pathogenic bacteria, viruses) refers to the amount of the compositions of the present invention required to achieve the desired result, e.g., reduce the overall number of infective agents, or reduce the severity and frequency of symptoms. The sufficient amount (or "therapeutically effective amount") can vary according to factors such as duration of treatment, severity of the infection, tolerance of the individual to treatment, and the type of infection.

An agent "interferes with infection" when it reduces the ability of an infective agent or pathogen to colonize the mucosal surface or penetrate the mucosal barrier, e.g., to infect host cells. For example, in the case of a pathogenic bacterium, an agent interferes with infection if it reduces the ability of the bacteria to adhere to and proliferate in the mucosal environment. In the case of a virus, however, an agent interferes with infection if fewer of the host cells are exposed to or infected by the virus. In either case, the reduction can be determined by comparison, e.g., to the individual before treatment or to a control individual exposed to similar conditions but not undergoing treatment.

B. Description of Lactobacillus crispatus Strain SJ-3C

The L. crispatus strain of the present invention was isolated from more than 200 Lactobacillus strains. The strain, and bacteria essentially derived from the parental strain, are called SJ-3C and have a number of advantageous and distinguishing characteristics.

The SJ-3C L. crispatus strain of the invention has at least five of the six following distinguishing characteristics: rapid growth in static medium having high magnesium concentrations (e.g., at least 10 mM); antagonism of pathogens that inhabit the vaginal mucosa (e.g., C. albicans); high viability during fermentation (e.g., higher than 90%); persistent colonization of mucosal surfaces; high viability even after desiccation and storage; and an easily detectable nucleotide tag. The following tests can be used to identify SJ-3C bacteria of the invention.

1. The SJ-3C strain grows rapidly in media comprising magnesium (e.g., 5, 10, 15, 20, 30, or higher mM concentrations of $Mg^{++}$). Addition of 10 mM $MgSO_4$ to standard MRS broth shortens the lag phase of SJ-3C bacteria grown statically at 37° C. with 5% $CO_2$. SJ-3C bacteria cultured for six hours in these conditions will produce 4 times as many bacteria, compared to non-Mg$^{++}$ conditions. Addition of 30 mM MgSO$_4$ also speeds growth of SJ-3C bacteria at 35° C. in a fermentor.

2. The SJ-3C strain produces H$_2$O$_2$ and is a potent antimicrobial agent. H$_2$O$_2$ production can be measured semi-quantitatively on MRS agar plates containing tetramethylbenzidine and horseradish peroxidase (Sigma-Aldrich, St. Louis, Mo., USA). MRS medium is not suitable for quantifying H$_2$O$_2$ production due to the presence of manganese that can catalyze the breakdown of H$_2$O$_2$ (Pridmore et al. (2008) *FEMS Microbiol Lett* 283:210-215; Marty-Teysset et al. (2000) *Appl Environ Microbiol* 66:262-267). Plates are incubated anaerobically at 37° C. for 24 hours and then exposed to ambient air at room temperature. Colonies are observed for color development (from white to blue, indicating H$_2$O$_2$ production) over time. SJ-3C was ranked among the strong H$_2$O$_2$ producers, based on its ability to produce H$_2$O$_2$.

The strain is capable of inhibiting a number of vaginal infective agents, including *C. albicans, Staphylococcus aureus*, and bacterial strains involved in vaginosis. As explained more detail in the Examples, overnight exposure of yeast to a spot of SJ-3C bacteria on MRS agar plates significantly inhibits growth of the yeast. Inhibition of growth is determined by the size of the "inhibition zone," where no yeast can be seen, surrounding the spot of SJ-3C bacteria. Compared to no inhibition of yeast growth in the absence of SJ-3C, a SJ-3C colony with a diameter of 10 mm produced a 16.7 mm diameter inhibition zone on the yeast lawn. For an entertoxin-F producing *Staphylococcus aureus* strain ATCC 51651, a SJ-3C colony with a diameter of 10 mm produced a 13.6 mm diameter inhibition zone on the *S. aureus* bacterial lawn 3. Ease of production is bolstered by the high % viability of SJ-3C bacteria after fermentation at 35° C. and pH 5, culture, and storage. As explained in the Examples, SJ-3C bacteria can be recovered at much higher % viability from culture than control *L. crispatus* strains. SJ-3C bacteria can also be recovered at high viability from media lacking a buffering agent. For example, SJ-3C bacteria grown into late log phase or stationary phase (8-12 hours) in MRS or Rogossa broth at 37° C. can be recovered at greater than 80% viability, while other *L. crispatus* strains are recovered in the range of 50% viability. SJ-3C bacteria also survive high temperatures better than many *L. crispatus* strains, as it persists in temperatures at least as high as 50-55° C. SJ-3C bacteria in standard MRS broth (with or without Mg$^{++}$) are 25-35% viable after 30 minutes at 50° C. About 5-10% of the SJ-3C bacteria are viable after 30 minutes at 55° C. in MRS broth with 10 mM Mg$^{++}$).

4. The present strain naturally colonizes vaginal mucosa. Colonization ability has been confirmed in Chinese rhesus macaques, where the bacteria are capable of persisting in a non-native environment for at least 10 days after final bacterial administration (see Examples).

5. SJ-3C in dried powder produced by freeze drying is recovered at high % viability (e.g., more than 20, 25, 30, 35, or 40%, such as 45%, 50%, 60%, 70%, 75% viability, or higher) in buffered preservation matrix after desiccation as well. Briefly, after SJ-3C bacteria were fermented in the Manufacture Medium to late log phase with pH control at 5.0 and glucose supplementation, the resulting cells were washed in PBS (pH 7.4), resuspended in the preservation matrix (5% skim milk, 5% trehalose, 2% xylitol, 0.1% sodium ascorbate, and 0.2% vitamin E in 20 mM sodium phosphate buffer, pH 7.4) and dried by freeze drying. The dried powder has about $6 \times 10^{10}$ CFU/g of SJ-3C live cells, determined immediately following drying.

6. The *Lactobacillus crispatus* strain of the invention is readily identifiable by the presence of a unique polynucleotide sequence comprising 819 nucleic acids (SEQ ID NO:1). Thus, the present strain can be identified by detecting a nucleic acid sequence with at least about 95% identity to the sequence of SEQ ID NO:1, e.g., 96%, 98% 99% or 100% identity.

Additional characteristics of SJ-3C can also be detected to aide in identification. The strain was designated as a *L. crispatus* strain based on the sequence of the 16S rDNA (see, e.g., Tannock et al. (2000) *Appl. Environ. Microbiol.* 66:2578-88). This sequence is provided in SEQ ID NO:2. SJ-3C bacterial cells are Gram-positive, asporogenous rods, which generally range from about 2.9 to 4.8 µM in length and 0.37 to 0.56 µm in width.

Characteristic of *L. crispatus*, SJ-3C ferments carbohydrate (primarily glucose) to produce lactic acid. SJ-3C, however, is able to utilize a very broad range of carbohydrates (see Examples). In standard culturing conditions, (static MRS broth incubated for 24 hours at 37° C. in 5% CO$_2$), SJ-3C produces at least 5.0 mg D-lactic acid/mL supernatant, and at least 3.8 mg L-lactic acid/mL supernatant. Similar to other *L. crispatus* strains, SJ-3C is able to grow at 37° C. in 5% CO$_2$, indicating that it is also capable of aerobic metabolism.

The parental SJ-3C strain was deposited with the American Type Cell Culture, 10801 University Blvd., Manassas, Va. 20110-2209 on Jun. 23, 2009, and granted accession number PTA-10138. This deposit was made in accordance with the Budapest Treaty and as described in 37 CFR 1.801-1.809.

C. Methods of Detecting the Distinguishing Characteristics of SJ-3C *L. crispatus*

Each of the distinguishing characteristics described herein can be detected according to standard methods known in the art. Additional exemplary assays are provided in the Examples section.

The identifying nucleotide tag of the SJ-3C strain can be detected by standard nucleic acid techniques, such as Southern blot, sequence analysis, electrophoresis, and PCR. For example, probes and primers can be designed using the sequence of SEQ ID NO:1. In addition, degenerate probes and primers can be used, e.g., to detect related or variant strains of SJ-3C. For a general overview of PCR, see PCR Protocols: A Guide to Methods and Applications. (Innis et al. eds.), Academic Press, San Diego (1990). For a general review of useful hybridization techniques, see "Current Protocols in Molecular Biology", 1991, Wiley (NY), Ausubel et al. eds. Sequences can be determined, e.g., by Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nat. Biotechnol.*, 16:381-384 (1998)), and sequencing by hybridization. Examples of electrophoretic analysis include slab gel electrophoresis such as agarose or polyacrylamide gel electrophoresis, capillary electrophoresis, and denaturing gradient gel electrophoresis.

Lactic acid levels can be determined, e.g., in culture media or other biological fluids, using a commercially available lactate meter (e.g., RQflex10 meter and Reflectoquant strips (Merk KGaA, Darmstadt, Germany)). Lactic acid can also be detected using common chemical separation techniques such as capillary electrophoresis and chromatography (e.g., HPLC).

Hydrogen peroxide ($H_2O_2$) production can be detected by any means for measuring $H_2O_2$ production. For example, $H_2O_2$ production can be semi-quantitated by the duration of time required for a blue pigment to develop when *Lactobacillus* grown under anaerobic conditions on a tetramethylbenzidine-containing medium (TMB) is exposed to air. $H_2O_2$ production can also be measured using commercially available $H_2O_2$ detection strips (e.g., available from Ozonelab or EM Sciences).

Viability and percent viability (e.g., after culturing or desiccation) can be determined visually, using a microscope. For example, a microscope with a dark field condenser and a Petroff-Hausser counting chamber can be used to obtain a total cell count. The live cell count can then be determined by colony forming units (CFU) on appropriate media plates, and the Live/Dead ratio calculated as CFU per ml/total cells per ml.

To determine colonization rate or to detect the present SJ-3C strain in an individual, a sample can be taken from the vaginal mucosa. Generally, a sample is taken by inserting a speculum into the vagina and swabbing the vaginal lining with a sterile swab. The sample is typically treated appropriately for the detection method to be used. For example, to analyze nucleic acids from the gathered cells, the swab is placed in PBS or a similar buffered liquid, and the cells are collected and lysed using standard methods. For observation of the cells, the sample can be applied to a glass slide and treated using standard methods (e.g., stained or fixed). Cell growth can be detected by applying the sample to an appropriate culture media, e.g., a media selective for *Lactobacillus*. An example of sample collection can be found, in Tamrakar et al. (2007) *BMC Infectious Diseases* 7:128.

D. Culturing Conditions

The *Lactobacillus* strain of the present invention can be grown in a number of different types of media, in either liquid, semisolid (e.g., agar), or solid form. The culturing conditions can be similar to the natural environment inhabited by the bacteria.

Standard bacterial media generally include salts, a source of carbohydrate, and a pH buffer. For *Lactobacillus*, pH is generally maintained in the range of about 4.5 to about 8.0 with the addition of sodium phosphate, arginine, ammonium hydroxide, sodium hydroxide, potassium hydroxide, etc. Lactobacilli are more acid-tolerant than many other types of bacteria, however SJ-3C bacteria can be grown even in media lacking buffer. Vitamins and growth agents, including amino acid formulations, can also be added. Bacterial media are known and commercially available (e.g., from Sigma-Aldrich). Media for use with the present strain include, e.g., MRS, Rogosa, NZM, YM, M17, Thayer-Martin, Trypticase Soy, and Brain-Heart infusion broth. Carbohydrates useful for growing the present strain include D-galactose, D-glucose, D-fructose, D-mannose, D-mannitol, N-acetylglucosamine, amygdalin, arbutin, esculin, salicin, D-cellobiose, D-maltose, sucrose, D-trehalose, amidon, and glycogen.

Selective media can be used to select for particular strains that tolerate the selective agent. For example, the present *L. crispatus* SJ-3C strain is resistant to lincomycin. Another example is *S. aureus*, a common infective agent, which grows in very high salt concentrations. Bacteria can be tolerant or genetically modified to tolerate antibacterial agents, as is known in the art.

*Lactobacillus crispatus* is a facultative anaerobe, which can use either aerobic or anaerobic (fermentative) metabolism depending the presence of $O_2$. $CO_2$ promotes SJ-3C growth, and is generally kept in the range of 0.1-10%, most commonly around 5%.

Lactobacilli naturally colonize mammalian mucosal surfaces, and generally grow optimally at about body temperature, i.e., 37° C. The SJ-3C strain, however, is thermotolerant, and can survive in temperatures at least as high as 55° C. Growth rate can be controlled by changing the temperature, e.g., growth is generally slower at temperatures less than 37° C.

The *Lactobacillus* strain of the invention is quite responsive to $Mg^{++}$, the addition of which results in a shorter lag phase for SJ-3C in static culture or at 35° C. when grown in a fermentor. Thus, media for rapid production of the present strain can include at least 1 mM $Mg^{++}$ (e.g., $MgCl_2$ or $MgSO_4$), e.g., 5 mM, 10 mM, 20 mM, 25 mM, 30 mM or 50 mM.

After reaching the desired cell density, the bacterial cells can be harvested using any suitable method to remove the cells from the culture media. Non-limiting exemplary methods for harvesting the cultured cells includes, filtration, centrifugation, and sedimentation. In some embodiments, the cell biomass is washed at least once using a physiologically balanced salt solution. In some embodiments, the wash solution may contain additional components, such as glucose. In some embodiments, the wash solution comprises a buffer or one or more buffering agents. Exemplary buffering agents that may be used or added to the wash solution include phosphate salts, (e.g., $Na_2HPO_4$, $NaH_2PO_4$, $NaHCO_3$, and arginine).

E. Formulations

Addition of a buffering agent to the bacterial preparation greatly enhances the stability and recovery of the bacteria following preservation, storage, and rehydration in an acidic environment. As discussed above, the cells can be washed with a buffer after removal from the culture medium and before formulation into a preservation matrix or pharmaceutical composition. In some embodiments, the buffering agent(s) can be added to the cell paste prior to suspension or formulation. In some embodiments, the buffering agent is added to the preservation matrix. In some embodiments, the buffering agent can be added to a dried bacterial preparation that does not yet comprise a buffering agent, or does not comprise sufficient buffering agent.

A buffering agent suitable for use with the present invention is a physiological agent, i.e., does not exert any toxic effects on the bacteria, vaginal epithelial cells, or a female patient using a pharmaceutical composition. In some embodiments, the buffering agent has a pKa of at least 4.2. In some embodiments, the buffering agent has a pKa of at least 4.3, 4.4, 4.5, 4.6, 4.7, 4.8, 4.9, 5.0, 5.5, 6.0, 6.5, 7.0, 7.5, 8.0, or higher. Exemplary buffering agents suitable for use with the present invention include $Na_2HPO_4$, $NaHCO_3$, phosphate salts, and arginine. In some embodiments, the buffering agent is present in a concentration range from about 6.25 mM to about 800 mM, e.g., about 6.25 mM, 12.5 mM, 25 mM, 50 mM, 75 mM, 100 mM, 125 mM, 150 mM, 175 mM, 200 mM, 250 mM, 300 mM, 400 mM, 500 mM, 600 mM, 700 mM, or 800 mM.

In some embodiments, the *Lactobacillus* strain of the invention is added to a preservation matrix to minimize the damaging effects of preservation process and to maintain functional properties. A suitable preservation matrix for use with the present invention can be any preservation matrix known in the art. For example, if the bacterial preparation is to be freeze dried, then the preservation matrix can include components known to protect against cryo-damage, such as trehalose or sucrose solutions. An exemplary preservation matrix suitable for use with the present invention is disclosed in U.S. Pat. No. 6,372,209. Other preservation matrices suitable for use with the present invention are disclosed in U.S. Pat. Nos. 5,614,209; 7,122,370; and 6,610,531.

In some embodiments, the preservation matrix acts to convert the bacteria from an actively growing metabolic state to a metabolically inactive state. The preservation matrix is formulated for optimal microbial cell resilience, such that upon rehydration (e.g., in situ), the microbial cells are immediately free to adhere to vaginal epithelial cells and then return to full metabolic activity.

In some embodiments, the preservation matrix maintains the bacteria for at least 12 months, at anywhere from 4-6° C. to room temperature, in vitro.

The preservation matrix can include a biologically active binding agent, an antioxidant, a polyol, a carbohydrate and/or a proteinaceous material. A biologically acceptable binding agent is any physiologically acceptable agent (e.g., does not have any biological activity or toxic effect in vivo) that affixes the cell matrix to an inert carrier during the preservative process and which provides protective effects (i.e., maintains cell viability) during preservation and storage. Biologically acceptable binding agents include water-soluble gum, carboxymethyl cellulose and/or gelatin. In some embodiments, the biologically acceptable binding agent comprises from about 5% to about 20% by weight of the preservation matrix. In some embodiments, a preservation matrix comprises about 6% gelatin by weight of the preservation matrix In some embodiments, the preservation matrix comprises an antioxidant to retard oxidative damage during the preservation and storage process. A suitable antioxidant is sodium ascorbate and vitamin E. In some embodiments, the antioxidant comprises from about 0.1% to about 1.0% by weight of the preservation matrix, e.g., about 0.1% sodium ascorbate and 0.2% vitamin E.

The preservation matrix can also comprise a polyol (i.e., polyhydric alcohol) to maintain the native, uncollapsed state of cellular proteins and membranes during the preservation and storage process. Suitable polyols include xylitol, adonitol, glycerol, dulcitol, inositol, mannitol, sorbitol and/or arabitol. In some embodiments, the preservation matrix comprises from about 1% to about 12% polyol by weight of the preservation matrix, e.g., about 6% xylitol.

The preservation matrix can also comprise a carbohydrate to maintain the native, uncollapsed state of cellular proteins and membranes during the preservation and storage process. Carbohydrates include trehalose, dextrose, lactose, maltose, sucrose, fructose and/or any other monosaccharide, disaccharide or polysaccharide. In some embodiments, the preservation matrix comprises from about 0.5% to about 5% carbohydrate by weight of the preservation matrix, e.g., about 5% trehalose by weight of the preservation matrix.

Proteinaceous materials can be added to protect the bacteria during dehydration. Exemplary proteinaceous materials include skim milk and albumin. In some embodiments, the preservation matrix comprises from about 0.5% to about 10% proteinaceous material by weight of the preservation matrix, e.g., about 5% skim milk.

In some embodiments, a suitable preservation matrix comprises a biologically active binding agent that is at least about 10% of the preservation matrix by weight, an antioxidant that is at least about 0.1% of the preservation matrix by weight, a polyol that is at least about 1% of the preservation matrix by weight, a carbohydrate that is at least about 0.5% of the preservation matrix by weight, and a proteinaceous material that is at least about 0.5% of the preservation matrix by weight. For example, the buffered preservation matrix can comprise: 6% gelatin, about 0.1% sodium ascorbate, 0.2% vitamin E, about 5% trehalose, about 5% skim milk and about 2% xylitol, by weight of the preservation matrix.

In some embodiments, the preservation matrix can include thickening agents, such as corn starch, guar gum, xantham gum, and the like. The preservation matrix can also include preservatives, for example, methylparaben, propylparaben, benzyl alcohol, and ethylene tetraacetate salts. The preservation matrix can also include a plasticizer such as glycerol or polyethylene glycol. Additional formulations and components are known in the art (see, e.g., WO05/034861).

F. Methods of Preservation and Storage

A vaginal medicant of the present invention can be a dried formulation. Numerous methods are known in the art for drying a bacterial preparation to increase their stability for long term storage. Typically the effect of drying is to place the bacteria in a state of dormancy to protect the bacteria from environmental elements that negatively impact the viability of the bacteria. The standard way to bring about dormancy is through the removal of water. Generally, sufficient water is removed so that the normal cellular processes (e.g. enzymatic activity) come to a halt or are at least greatly diminished.

A dried formulation of the present invention has less than about 5% moisture content. In some embodiments, the water content of the dried formulation is less than about 5%, 4%, 3%, 2%, 1%, or less. Water content in a *Lactobacillus* powder can be determined gravimetrically after drying at 105° C. for 24 hours. Alternatively, an instrument for measuring water content in powders could be used to monitor the moisture content of the formulation during drying, e.g., the IR-120 Moisture Analyzer (Denver Instruments, Denver, Colo.). Water content in a *Lactobacillus* powder can also be measured as water activity (Aw) using a water activity meter, e.g., a Decagon AquaLab Model series (Decagon Instruments, Pullman, Wash.), or a Rotronic Model series (Rotronic Instrument Corp., Huntington, N.Y.).

Numerous methods are known in the art for drying bacterial preparations. Drying methodologies and protective agents are disclosed in the review by Morgan et al. (2006) *J. Microbiol. Meth.* 66:183-193. Suitable drying methods include air drying, vacuum drying, oven drying, spray drying, flash drying, fluid bed drying, controlled atmosphere drying, and freeze drying (i.e., lyophilization). In some embodiments, a desiccant is used to aid in the drying process, and/or to prevent resorbtion of moisture into the dried formulation. In some embodiments, the drying is carried out using a fluid bed dryer. In some embodiments, the drying is carried out using a spray dryer.

The *Lactobacillus* strain of the present invention is thermotolerant, and maintains viability across a wider than normal range of temperatures. This can be important for drying, where temperatures can range from about 40° C. to about 140° C. In some embodiments, the relative humidity of the air flow is in the range from about 30% to 0%.

The formulation can be coated onto an inert carrier, e.g., a maltodextrin bead. The coated beads are then dried, e.g., by a fluid bed drying method. Fluid bed drying methods are well known in the art. In some embodiments, maltodextrin beads are placed into a fluid bed dryer and dried at 33° C. The air pressure is set to 14 psi, the formulation is sprayed onto the beads and the temperature is increased to 38° C. The coated beads are then allowed to dry for an additional period of time, until the desired amount of water has been removed. The dried coated maltodextrin beads can be stored as a powder, placed into gelatin capsules, or pressed into tablets.

Cells suspended in preservation matrix can be spray-dried onto a maltose dextrin seed in a 300N fluid bed drier (Applied Chemical Technology, Inc.). In some embodiments, a Buchi Mini spray drier B-290 (Buchi Laboratory Equip. Zurich Switzerland) is used. In some embodiments, cell suspensions in a buffered preservation matrix can be dried in a freeze dryer. In some embodiments, the maltose dextrin accounts for approximately 70% of the dried powder.

A rehydration formulation to facilitate the rehydration of the bacteria can be included with a preservation matrix or dried formulation. Non-limiting exemplary components of a rehydration formulation can include glucose, potassium citrate, sodium chloride, and sodium citrate.

A suppository format comprising a gelatin capsule can be used for delivering bacterial cells of the vaginal medicant to the vaginal milieu. Gelatin or vegetable-based capsules are commercially available and are well known in the art. Bacterial cells suspended in the preservation matrix comprising at least one buffering agent can be dispensed into a gelatin or vegetable-based capsule, which is then chilled (e.g., at about 4-6° C.) until the cell suspension matrix forms a non-fluid matrix affixed to the interior wall of the capsule. The capsule can then be desiccated in a desiccation chamber. The step of desiccating the gelatin capsule can include the steps of (i) providing dry air to the desiccation chamber containing less than about 25% moisture, at a temperature from about 24° C. to about 32° C.; and (ii) removing humidified air from the desiccation chamber.

The delivery compositions can be packaged to protect against moisture and oxygen during transport and storage. The package can be comprised of any suitable material for such protection such as Mylar or metallic film pouches. In some embodiments, the delivery compositions are sealed into individual packages, e.g., for individual dosages. In other embodiments, a single package may comprise multiple cavities. In some embodiments, a package with multiple cavities can comprise the same or different doses of the composition.

G. Dosage and Administration

The *Lactobacillus* strain of the present invention maintains high percentage viability in a number of conditions, including culture, preservation (e.g., drying), and long-term storage. The number of viable, substantially pure, genetically stable cells that are delivered in a single dose (e.g., a single suppository or tablet) is directly related to the issue of potency of a bacterial formulation. The formulations of the present invention are efficacious in situ by allowing for colonization of the vaginal mucosa by at least about $10^6$ cells of the present *Lactobacillus* strain and/or a biological effect (e.g., alleviation or prevention of an infected state such as bacterial vaginosis, urinary tract infection, and yeast vaginitis). There can be a difference between the potency of a formulation that allows colonization of the suppository strain and the potency of a formulation that provides a biological effect. Thus, generally, the ability of a vaginal medicant formulation of the invention to colonize vaginal epithelial cells is combined with the specific potency requirements for a biological effect. For example, colonization of vaginal epithelial cells can be achieved at very low potencies (e.g., $10^5$ cells) using the present *Lactobacillus* strain.

The dosage and frequency of administration depend on a number of factors, as will be appreciated by one of skill in the art. The severity of the infection or risk of infection can affect the dosage and frequency of administration. For example, an individual with a history of recurring vaginosis may require a higher dose and/or more frequent administration than an individual at relatively lower risk of vaginal infection. Another factor to be considered is mode of administration. Dose and administration can also vary widely from individual to individual, based on, e.g., history of infection by vaginal pathogens, age and size, and the individual vaginal milieu (e.g., pH, additional vaginal flora). Generally an individual will begin treatment at a relatively low dose and/or frequency, and track the efficacy of the regimen for reducing vaginal infection. One of skill in the art will be readily able to determine optimal dosage, route of administration, and frequency of administration without undue experimentation.

A therapeutically effective amount of vaginal medicant generally includes from about $10^6$ to about $10^{12}$ colony forming units (CFUs) per administration (dose) of the *Lactobacillus* strain of the invention. In some embodiments, a therapeutically effective dose ranges from about between about $10^7$ to about $10^{11}$ CFUs per administration. In some embodiments, a therapeutically effective dose ranges from about $10^8$ to about $10^{10}$ CFUs per administration. As explained above, CFUs indicate the number of viable bacterial cells.

In some embodiments, the number of administrations ranges from about 1 to about 6 administrations per day. In some embodiments about 2 to about 3 administrations per day are required to achieve the desired effect. In some embodiments, the overall amount of viable bacteria administered per day is from about $10^6$ to about $10^{12}$ CFUs per day. In some embodiments, between about $10^7$ and about $10^{11}$ CFUs are administered per day. In some embodiments, about $10^8$ to about $10^{10}$ CFUs are administered per day.

In some cases, e.g., for the prophylactic purposes, administration is less frequent. For example, administration can be linked to menstrual cycle, and taken only a few times a month. In some cases, administration can be episodal, e.g., during times of increased sexual activity or other exposure to pathogens.

H. Detection of Pathogens

The *Lactobacillus* strain of the present invention is effective for reducing the survival of and/or inhibiting infection by a number of pathogens that infect or gain entry through mucosal surfaces. In particular, the SJ-3C strain is effective for reducing the growth of pathogenic yeast and bacteria in the vaginal mucosa. The presence of SJ-3C strain in vaginal ecosystem can also reduce a woman's risk of acquiring viruses that enter via vaginal contact, such as HIV (human immunodeficiency virus), HPV (human papilloma virus), and HSV (herpes simplex virus) (see, e.g., Martin et al. (1999) *J. Infect. Dis.* 180:1863-68).

Detection of vaginal pathogens is useful for accurate diagnosis and for monitoring the progress of therapy according to the present invention. Detection methods for the vaginal pathogens targeted by the present invention are generally straightforward and well known in the art. Such infections can often be detected by a woman without medical consultation or diagnostic apparatuses or kits. Symptoms generally include abnormal odor and/or discharge, and discomfort from itching and/or pain.

A number of inexpensive, non-prescription kits for detecting yeast are available (e.g., Vagisil™). Alternatively, specific yeast strains can be detected using PCR (see, e.g., Ruzicka et al. (2005) *Clin Microbiol Inf* 11:481; Ahmad et al. (2002) *J Clin Microbiol* 40:2483-89).

Bacterial vaginosis can be detected, e.g., by Amsel clinical criteria or Gram stain, as performed with a standard Pap smear. PCR methods can be employed for detection of particular strains (see, e.g., Fredricks et al. (2007) *J Clin Microbiol* 45:3270-76; Nierengarten, "PCR Assays Improve Diagnosis of Bacterial Vaginosis," *Medscape Medical News* (Oct. 10, 2005), available at medscape.com). Trychomonas is also commonly detected by PCR or ELISA (Hobbs et al. (2006) J Clin Microbiol 44:3994-99; Jeremias (1994) *Inf Dis Obstetrics Gyn* 2:16-19). Medical practitioners can also check for common vaginal pathogens using automated systems (e.g., BD Microbial Identification).

*Chlamydia* and gonorrhea can be detected in routine STD tests, e.g., using vaginal swabs. Similarly, viral pathogens are frequently included in STD tests.

Viral detection generally requires a blood or tissue sample, but can rely on saliva (e.g., Orasure®), vaginal swab, or urine. For example, HIV and herpes are commonly diagnosed by detecting antibodies to the virus that are present in these fluids using an ELISA or Western blot. HPV is most commonly diagnosed during routine Pap smear, by detection of abnormal cervical cells.

Successful prophylactic and treatment regimes reduce the ability of a pathogenic agent to infect the individual (i.e., neutralize or partially neutralize the pathogen). In the case of yeast and bacterial agents, the term "reducing infection" generally refers to reducing the ability of the pathogen to inhabit or survive on the mucosal surface. In the case of viral pathogens, the term refers to a reduced ability of the viral particle to infect the cells of the individual and promote an immune response. This reduced infective ability can result from reduced viability of the virus, e.g., to survive long enough to bind to or penetrate target cells.

It is understood that the examples and embodiments described herein are for illustrative purposes only and that various modifications or changes in light thereof will be suggested to persons skilled in the art and are to be included within the spirit and purview of this application and scope of the appended claims. All publications, websites, patents, and patent applications cited herein are hereby incorporated by reference in their entireties for all purposes.

I. Examples

The human vaginal ecosystem harbors a complex microflora. Lactobacilli are dominant within the microflora of healthy women, and have been shown to adhere tightly to vaginal epithelial cells in vitro. Most healthy women are predominantly colonized by either *L. crispatus, L. gasseri*, or *L. jensenii*. The *L. crispatus* strain of the invention was found to have a number of advantageous distinguishing characteristics. These include ease of production and storage, antagonism of pathogens, and persistent colonization of mucosa.

1. SJ-3C can be Easily Grown In Vitro

Ease of production was demonstrated by the high % viability of SJ-3C bacteria. SJ-3C and a control *L. crispatus* strain (CTV-05) were cultured in MRS broth at 37° C. with 5% $CO_2$ to late log phase or stationary phase (for 8-12 hours). SJ-3C was recovered at 82% viability, while CTV-05 was only 50% viable. SJ-3C also survived well in Rogossa medium, even in the absence of buffering capacity (92% vs 89%, respectively).

SJ-3C was found to grow rapidly in media supplemented with magnesium. SJ-3C was cultured statically without shaking in MRS media in the presence or absence of magnesium (10 mM $Mg^{++}$). In the presence of $Mg^{++}$, the lag phase lasted only 3 hours, as compared to 7 hours without $Mg^{++}$. After 6 hours, 4 times as many SJ-3C bacteria were present in the culture with $Mg^{++}$ than in the culture with no $Mg^{++}$.

SJ-3C could be readily fermented using BioFlo 110 Microbial Fermentor, in 1.2 L of Manufacturing Medium with 0.02% Trans-280, pH controlled at 5 by the addition of 2M $NH_4OH$, at 35° C. or 37° C., with or without glucose supplementation and $MgSO_4$ addition. Live/dead ratios of SJ-3C cells in late log phase/early stationary phase fermented under these conditions are at least 90%. The results are summarized in Table 1. The Manufacturing Medium contains: BD Difco Select Soytone (7 g/L), BD Bacto Yeast Extract (18 g/L), Tween 80 (1 g/L), Dextrose (20 g/L), anhydrous sodium acetate (4.5 g/L), anhydrous dipotassium phosphate (1.8 g/L), diammonium citrate (1.8 g/L), anhydrous magnesium sulfate (0.2 g/L), monohydrate manganese sulfate (0.056 g/L), and Trans-280 (0.2 g/L).

TABLE 1

Live/dead ratio of fermented SJ-3C cells under different conditions

| Fermentation conditions | Time point (hr) | $OD_{600}$ | Number of Live Cells (CFU/ml) | Live/dead ratio |
|---|---|---|---|---|
| No glucose, no pH control at 37° C. | t = 7 | 4.9 | $3.89 \times 10^8$ | 77.8% |
| pH 5, no glucose at 37° C. | t = 8.5 | 8.9 | $1.55 \times 10^9$ | 96.9% |
| pH 5 + glucose supplementation at 37° C. | t = 8.5 | 12 | $3.22 \times 10^9$ | 96.1% |
| pH 5 + glucose + 10 mM $MgSO_4$ at 37° C. | t = 9 | 9.9 | $2.50 \times 10^9$ | 92.6% |
| pH 5 + glucose + 30 mM $MgSO_4$ at 37° C. | t = 9 | 10.38 | $3.98 \times 10^9$ | 90.5% |
| pH 5, no glucose at 35° C. | t = 8.5 | 8.4 | $1.61 \times 10^9$ | 100% |
|  | t = 7.5 | 8.7 | $1.70 \times 10^9$ | 99.2% |
| pH 5 + glucose at 35° C. | t = 7.5 | 8.2 | $1.77 \times 10^9$ | 93.0% |
| pH 5 + glucose + 30 mM $MgSO_4$ at 35° C. | t = 7 | 9.0 | $2.15 \times 10^9$ | 91.6% |

SJ-3C is also thermotolerant and persists at temperatures well above 37° C. SJ-3C and a control *L. crispatus* strain (CTV-05) were cultured in MRS broth as outlined in Table 2 below. Survival was determined as a percentage of viability (CFU/ml) at 37° C.

TABLE 2

In vitro thermotolerant property of *L. crispatus* SJ-3C after exposure to different temperatures for 30 minutes

| Temperature | CTV-05 (%) | | SJ-3C | |
| --- | --- | --- | --- | --- |
| | No Mg | 10 mM Mg | No Mg | 10 mM Mg |
| 37° C. | 100% | 100% | 100% | 100% |
| 50° C. | 0.0015% | 0.0375% | 25% | 30% |
| 55° C. | ND | 0.00025% | 0.2% | 6.7% |

The ability of SJ-3C to ferment and survive on different carbohydrate sources was tested using the Api® 50C14 panel (bioMeriux®, Inc., Durham, N.C.). A panel of 50 carbohydrates was tested. SJ-3C was grown in standard media and added to the provided microtubes with each of the sugar sources, according to the included protocol. Fermentation was determined using a colorimetric pH assay (bromcresol purple). SJ-3C was capable of fermenting 16 of these carbohydrate sources to at least some extent. These included: D-galactose, D-glucose, D-fructose, D-mannose, D-mannitol, N-acetylglucosamine, amygdalin, arbutin, esculin, salicin, D-cellobiose, D-maltose, sucrose, D-trehalose, amidon, and glycogen.

2. SJ-3C Inhibits Growth of Yeast and *Staphylococcus* Cells In Vitro

*Lactobacillus crispatus* strains were spotted in the center of MRS agar plates and grown anaerobically for 48 hours at 37° C. The strains tested were SJ-3C, CTV05, SV-10A, and SV-40. The lactobacilli were overlaid with melted YM agar containing yeast (*Candida albicans*) cells. After solidification of the agar overlay, plates were incubated at 37° C. overnight in the 5% CO2 incubator. Inhibition of yeast growth was indicated by the size of the inhibition zone surrounding the lactobacilli spots. SJ-3C inhibited the growth of yeast cells more effectively than the other strains. For each 10 mm diameter *lactobacillus* spot, the inhibition zone (diameter in mm) of SJ-3C, CTV-05, and SV10A were 16.7, 13.8, and 11.2, respectively.

*Lactobacillus crispatus* strains were spotted in the center of LAPTg agar plates and grown anaerobically for 24 hrs at 37° C. The strains tested were SJ-3C and CTV05. The lactobacilli were overlaid with melted LAPTg agar containing *Staphylococcus aureus* ATCC 51651 (enterotoxin-F producing) cells. After solidification of the agar overlay, plates were incubated at 37° C. overnight in the 5% $CO_2$ incubator. Inhibition of *S. aureus* growth was indicated by the size of the inhibition zone surrounding the lactobacilli spots. Per each 10 mm-diameter lactobacilli spot, the inhibition zones (diameter in mm) of SJ-3C and CTV-05 were 13.6 and 14.4, respectively.

3. Antibiotic Resistance of SJ-3C

Antibiotic susceptibility and resistance of SJ-3C was tested by the agar overlay disc diffusion method. SJ-3C cells were mixed in melted MRS agar and overlaid on MRS agar plates. After solidification of the agar overlay, BBL Sensi-Disc Antimicrobial Susceptibility Test Discs manufactured by BD were placed on top of the agar overlay. Plates were incubated at 37° C. overnight anaerobically. Clearance zones around the discs (diameter to the nearest mm) were measured on the lawn of bacteria. Among the 19 tested antibiotics, SJ-3C demonstrated resistance to some of them, including: lincomycin, metronidazole, gentamicin, fosfomycin, sulfisoxazole, sulfamethoxazole-trimethoprim, and ciprofloxacin.

4. SJ-3C Colonizes Vaginal Mucosa

The ability of SJ-3C to colonize vaginal mucosa was tested in Indian rhesus macaques. SJ-3C were mixed with hydroxyethyl cellulose (HEC) and administered vaginally at a dose of 109 CFU per day for five days. Vaginal swabs were collected for quantitative microflora analysis. The results of SF-3C colonization levels are described in Table 3.

TABLE 3

Level of *L. crispatus* SJ-3C recovered from vaginal swabs collected from four Indian rhesus macaques

| Test animal | 3 days after final dose (CFU/vaginal swab) | 10 days after final dose (CFU/vaginal swab) |
| --- | --- | --- |
| 1 | $8.0 \times 10^6$ | $3.2 \times 10^5$ |
| 2 | $4.8 \times 10^7$ | $2.8 \times 10^7$ |
| 3 | $2.0 \times 10^6$ | $4.0 \times 10^6$ |
| 4 | $1.0 \times 10^8$ | $2.0 \times 10^7$ |

As shown above, the SJ-3C bacteria were able to compete with the native vaginal microflora of Indian rhesus macaques and colonize the mucosal surface.

J. Informal Sequence Listing

SEQ ID NO:1 Nucleotide sequence unique to *Lactobacillus crispatus* SJ-3C strain (819 nucleotides)

GGCCTACAAGACAAATCCAGAGTTGAATAACTTTGTAAATCGAATTATGC

AAAAAGGTACTCCTGAATATAACGCTTTAGGTGATGGTATTGGTACATTT

CAAAATACTGATACCTTAGCTAAATTTTTACCTAAATTAAAGGCGTTAGG

AATGGATAGTGCGAGAAGTCTTAATGATTTAGATGCCTTCAGATATAATA

ATGTGAAACAGCACTTCATTAATCTAAAAGAAAGAGATCCCAAGAAAGTC

GCAGATGAAATCTTTAATGCTTATACAAGAGAAGAAGACAACATAGACTT

GAGAACACTTGAAGGACATAAAGATAAATATGCTTATGCTGCTTTAAAAG

TTAGATTCAATAATGAGGGAGATTATATCGATCACGGTTTGGAATTAAAC

TTTACCGTTGTAGGAAGTTATTCACCAGAATGGATTAAGGCTTGGGAAGC

TGCTAAGTAGAAATTAGAAATAAAGGTTAATTAGTTATGCTAATTGCCTT

TTTTTGTTCCTAAAAATGAAAATAAAAAAAAGTAGATTAGCTATTAATCA

ACAGCGAAAAGTGATAAAAGAAAAAAATTGGTACAATAGTAGCTATTG

TTGCACTAATTTTAATCGGGGTTGCGATTTACTGTATTGCAAACTTTAAT

CATCTTCAAGGAAAAGCTGCTAACTATGTAGCAACTAATCATTTGTCGAG

TCAAAGAAAAAACAAACAGAAGAAAAAGCCAAGTTTTAATATGAAGGCTG

TCCAACCTGTATCACCTCAATCTCTTGCCAATGCATATCAGCATAGAAGA

GATTATCGAGCTGTAGGCC

SEQ ID NO:2 Partial sequence of 16S rDNA gene of *Lactobacillus crispatus* SJ-3C strain (1.528 kb)

AGAGTTTGATCATGGCTCAGGACGAACGCTGGCGGCGTGCCTAATACATG

CAAGTCGAGCGAGCGGAACTAACAGATTTACTTCGGTAATGACGTTAGGA

AAGCGAGCGGCGGATGGGTGAGTAACACGTGGGGAACCTGCCCCATAGTC

```
TGGGATACCACTTGGAAACAGGTGCTAATACCGGATAAGAAAGCAGATCG
CATGATCAGCTTTTAAAAGGCGGCGTAAGCTGTCGCTATGGGATGGCCCC
GCGGTGCATTAGCTAGTTGGTAAGGTAAAGGCTTACCAAGGCGATGATGC
ATAGCCGAGTTGAGAGACTGATCGGCCACATTGGGACTGAGACACGGCCC
AAACTCCTACGGGAGGCAGCAGTAGGGAATCTTCCACAATGGACGCAAGT
CTGATGGAGCAACGCCGCGTGAGTGAAGAAGGTTTTCGGATCGTAAAGCT
CTGTTGTTGGTGAAGAAGGATAGAGGTAGTAACTGGCCTTTATTTGACGG
TAATCAACCAGAAAGTCACGGCTAACTACGTGCCAGCAGCCGCGGTAATA
CGTAGGTGGCAAGCGTTGTCCGGATTTATTGGGCGTAAAGCGAGCGCAGG
CGGAAGAATAAGTCTGATGTGAAAGCCCTCGGCTTAACCGAGGAACTGCA
TCGGAAACTGTTTTTCTTGAGTGCAGAAGAGGAGAGTGGAACTCCATGTG
TAGCGGTGAAATGCGTAGATATATGGAAGAACACCAGTGGCGAAGGCGGC
TCTCTGGTCTGCAACTGACGCTGAGGCTCGAAAGCATGGGTAGCGAACAG
GATTAGATACCCTGGTAGTCCATGCCGTAAACGATGAGTGCTAAGTGTTG
```

```
GGAGGTTTCCGCCTCTCAGTGCTGCAGCTAACGCATTAAGCACTCCGCCT
GGGGAGTACGACCGCAAGGTTGAAACTCAAAGGAATTGACGGGGGCCCGC
ACAAGCGGTGGAGCATGTGGTTTAATTCGAAGCAACGCGAAGAACCTTAC
CAGGTCTTGACATCTAGTGCCATTTGTAGAGATACAAAGTTCCCTTCGGG
GACGCTAAGACAGGTGGTGCATGGCTGTCGTCAGCTCGTGTCGTGAGATG
TTGGGTTAAGTCCCGCAACGAGCGCAACCCTTGTTATTAGTTGCCAGCAT
TAAGTTGGGCACTCTAATGAGACTGCCGGTGACAAACCGGAGGAAGGTGG
GGATGACGTCAAGTCATCATGCCCCTTATGACCTGGGCTACACACGTGCT
ACAATGGGCAGTACAACGAGAAGCGAGCCTGCGAAGGCAAGCGAATCTCT
GAAAGCTGTTCTCAGTTCGGACTGCAGTCTGCAACTCGACTGCACGAAGC
TGGAATCGCTAGTAATCGCGGATCAGCACGCCGCGGTGAATACGTTCCCG
GGCCTTGTACACACCGCCCGTCACACCATGGGAGTCTGCAATGCCCAAAG
CCGGTGGCCTAACCTTCGGGAAGGAGCCGTCTAAGGCAGGGCAGATGACT
GGGGTGAAGTCGTAACAAGGTAACCGTA
```

What is claimed is:

1. An isolated *Lactobacillus crispatus* SJ-3C strain deposited under ATCC number PTA-10138.

2. A pharmaceutical composition comprising the *Lactobacillus* of claim 1.

3. The pharmaceutical composition of claim 2, wherein the *Lactobacillus* are desiccated.

4. The pharmaceutical composition of claim 3, wherein the *Lactobacillus* are at least 20% viable upon rehydration from desiccated conditions.

5. The pharmaceutical composition of claim 2, wherein the composition is a dried formulation.

6. The pharmaceutical composition of claim 2, wherein the pharmaceutical composition comprises a preservation matrix comprising a binding agent, an antioxidant, a polyol, a carbohydrate, and a proteinaceous material.

7. The pharmaceutical composition of claim 2, wherein the composition is in a single dosage form appropriate for vaginal delivery.

8. The pharmaceutical composition of claim 7, wherein the single dosage form comprises at least $10^8$ viable *Lactobacillus* of claim 1 for at least 12 months in vitro.

9. The pharmaceutical composition of claim 7, wherein the single dosage form comprises at least $10^8$ viable *Lactobacillus* of claim 1 for at least 12 months at a temperature of 4-6° C.

10. The pharmaceutical composition of claim 7, wherein the single dosage form comprises at least $10^8$ viable *Lactobacillus* of claim 1 for at least 12 months at room temperature.

11. A method of growing the *Lactobacillus* crispatus SJ-3C strain of claim 1, the method comprising the step of growing the *Lactobacillus* with media comprising 10-30 mM magnesium.

* * * * *